(12) United States Patent
Filer

(10) Patent No.: US 7,323,566 B2
(45) Date of Patent: Jan. 29, 2008

(54) RADIOPHARMACEUTICAL AND METHODS OF SYNTHESIS AND USE THEREOF

(76) Inventor: Crist N. Filer, 14 Bow Street Pl., Somerville, MA (US) 02143

( * ) Notice: Subject to any disclaimer, the term of this patent is extended or adjusted under 35 U.S.C. 154(b) by 0 days.

(21) Appl. No.: 11/110,279

(22) Filed: Apr. 20, 2005

(65) Prior Publication Data

US 2005/0261266 A1 Nov. 24, 2005

Related U.S. Application Data

(60) Provisional application No. 60/521,425, filed on Apr. 23, 2004.

(51) Int. Cl.
*C07D 221/18* (2006.01)
*A61K 51/00* (2006.01)

(52) U.S. Cl. .................. 546/75; 424/1.37; 424/9.1; 546/48; 514/284

(58) Field of Classification Search ............... 546/75, 546/48; 424/1.37, 9.1; 514/284
See application file for complete search history.

(56) References Cited

OTHER PUBLICATIONS

Simon, C. et al.: Synthesis of C-3 halogen-substituted apocodeines and apomorphines. Synthetic Commun. vol. 21, pp. 2309-2316, 1991.*
Hussain, S.F. et al.: A new pentasubstituted aporphine: (+)-N-methyldanguyelline. J. of Natural Products, vol. 52, pp. 428-429, 1989.*
Sheppard, H. et al.: The dopamine-sensitive adenylate cyclase of the rat caudate nucleus. Biochemical Pharmacol. vol. 27, pp. 1113-1116, 1978.*
Vasdev et al., Selectivity of [F]F2 towards L—Methyltyrosine and L-Tyrosine: A Radiochemical and NMR Spectroscopic Study; J. Labelled Cpd. Radiopharm 44, Suppl.1 2001 S863-S865.
2004 American Chemical Society; pp. 1-29; Absolute Chemistry.
Ajao et al., The Preparation and Oxidative Dimerisation of 2-Acetyl-7-hydroxy-1,2,3,4-tetrahydroisoquinoline Synthesis; Dept. of Chem, Queen Elizabeth College, London,EnglandMar.-Apr. 1984; pp. 329-331.
Langer et al.,Preparation of 4- and 6- [Br]Bromometaraminol, Two Pet Tracers for the Adrenergic Nerve Sysem, J. Labelled Cpd. Radiopharm 40, (1997) 117-119.
DeVos et al., Synthesis of Iodoaminoglutethimide, a Possible Radioligand for the Visualisation of the Aromatase Enzyme in Breast Carcinoma by Spect, J. Labelled Cpd. Radiopharm 40, (1997) 375-376.
C Loc'h et al, Preparation and Preliminary Evaluation of 3-threo Bromomethylphenidate Enantiomers; Potential Tracers for PET Study of Dopamine Reuptake Sites, J. Labelled Cpd. Radiopharm 42, (1999) S42-S44.
Pacer et al., Synthesis of 1-(3-[F]Fluorobenzly)-4-[2(N-Phthalimid-1-yl)Ethyl] Piperidine, J. Labelled Cpd. Radiopharm 44, Suppl.1 (2001); S920-921.

Constantinou et al., Improved Preparation of [F] Xenon Difluoride from [F] Fluoride for Labelling Reactions; J. Labelled Cpd. Radiopharm 42, Suppl 1 (1999), S530-532.
Filer et al., Preparation of (−)-[8,9-H]Apomorphine at High Specific Activity, Journal of Organic Chemistry 1980, 45, 3918-3919.
Cramer et al., Gas Phase Fluorination of Benzene, Fluorobenzene, m-Difluorobenzene and Trifluoromethylbenzene by Reactions of Thermal Fluorine-18 Atoms, Dept of Chemistry, University of CA, Irvine, CA Mar. 12, 1974, 6579-6584.
Berenyi et al.,A New Efficient Method for the Preparation of 2-Fluoro-N-propylnorapomorphine, J.Chem. Soc. Perkin Trans, Jan. 1992, 2693-2694.
Fuchtner et al., 3-O-Methyl-6-[F]Fluoro-L-Dopa-A Promising Substance for Tumour Imaging, J. Labelled Cpd. Radiopharm 42, Suppl. 1 (1999), S267-269.
John et al., Synthesis, Characterization and Initial Clinical Evaluation of 3-[123I]Iodo-N-[2-(1-Piperidinyl) Ethyl]4-Methozybenzamide, [123I] Pimba in Breast Cancer Patients,J. Labelled Cpd. Radiopharm. 42, Suppl. 1 (1999) S261-263.
Nagasawa et al., Synthesis and Dopamine Receptor Affinity of (R)-(−)-2Fluro-N-n-propylnorapomorphine: A Highly Potent and Selective Dopamine D Agonist, J. Med. Chem. 1990, 33, 3122-3124.
Baldessarini et al., R(−) Fluoro-N-Propylnorapomorphine a very Potent and D2-Selective Dopamine Agonist, Neuropharmacology, vol. 30, No. 1, 97-99, 1991.
Vasdev, Synthesis of Fluorine-18 Labeled 5—Fluoro-L-Dopa by Direct Fluorination of L-Dopa, J Labelled Cpd. Radiopharm, 42, Suppl 1(1999), S486-488.
Windhorst et al., Radiosynthesis and Biodistribution of I Labeled Antagonists as Potential Spect Ligands for the Histamine H3 Receptor, J. Labelled Cpd. Radiopharm, 42, Suppl. 1 (1999), S282-283.
Gillings et al., An Improved Synthesis and Evaluation in Pig Brain of the Dopamine Agonist Ligand: R-[N-Methyl-C] Apmorphine, J. Labelled Cpd. Radiopharm, 44, Suppl. 1(2001), S210-212.
Ramsby et al., 2-Haloaporphines as Potent Dopamine Agonists, J. Med. Chem 1989, 32, 1198-1201.
Morin et al., N-Monofluoroalkylnoraporphines Synthesis and Binding Dopamine Receptor Studies, Med. Chem Res (1992) 2:354-360 1992.
Tierling et al., A New Nucleophilic Asymmetric Synthesis of 6-[F] Fluoro-Dopa, J. Labelled Cpd. Radiopharm. 44, Suppl. 1 (2001), S146-147.
Weisbach et al., Studies in the Synthesis and Pharmacology of Aporphines, Journal of Medicinal Chemistry, vol. 6, No. 2, Mar. 6, 1963, 91-97.
Zijlstra et al., Synthesis and In Vivo Distribution in the Rat of Several Fluorine-18 Labeled N-Fluoroalkylaporphines, Appl. Radiat. Isot. vol. 44, No. 4, 651-658, 1993.

(Continued)

*Primary Examiner*—Charanjit S. Aulakh
(74) *Attorney, Agent, or Firm*—Gifford, Krass et al.

(57) ABSTRACT

A novel group of apomorphine derivatives are provided that are well suited as radioimaging agents upon incorporation of radionuclides. Through reaction of D ring sites, the less reactive sites of the apomorphine A ring is modified in ways previously unattainable.

27 Claims, No Drawings

OTHER PUBLICATIONS

Cumming et al., Kinetics of the uptake and distribution of the dopamine D2,3 agonist (R)-N-[1-11C]n-propylnorapomorphine in brain of healthy and MPTP-treated Bottingen miniature pigs, Nuclear Med and Bio 30 (2003) 547-553.

Filer et al., Isoquinolines.7.Reaction of Ethylene Oxide with Ioquinolines. Novel Isoquinolone and Oxazolidine Formation, J. of Organic Chemistry 43, 672 (1978), 673-678.

Filer et al, Aporphines. 28.Preparation of (−)-N-n[3H-and-2H] Propylnorapomorphine, J. Org. Chem. 1980, 45, 3465-3467.

Koziorowski et al., Rapid Preparation of 5-[I]iodo-2-Deoxyuridine by iododestannylation, J. Labelled Cpd. Radiopharm 40, 128 (1997).

Argiolas et al., N-n-Propyl-Norapomorphine: An Extremely Potent Stimulant of Dopamine Autoreceptors, Brain Research, 231 (1982) 109-116.

Hwang et al., (−)-N[C] Propyl-Norapomorphine: A Positron-Labeled Dopamine Agonist for PET Imaging of D2 Receptors, Nuclear Medicine & Biology, vol. 27, pp. 553-539, 2000.

Halldin et al., PET Studies with Carbon-11 Radioligands in Neuropsychopharmacological Drug Developement, Current Pharmaceutical Design, 2001, 7, 1907-1929.

\* cited by examiner

RADIOPHARMACEUTICAL AND METHODS OF SYNTHESIS AND USE THEREOF

RELATED APPLICATION

This application claims priority of U.S. Provisional Patent Application Ser. No. 60/521,425 filed Apr. 23, 2004, which is incorporated herein by reference.

FIELD OF THE INVENTION

The present invention in general relates to apomorphic derivatives and in particular to apomorphic derivatives operative as radioimaging agents.

BACKGROUND OF THE INVENTION

Dopamine receptors mediate signals that regulate neuronal function, and thereby have important roles in physiological processes governed by neuronal function. The absence of normal dopamine receptor expression, excessive expression of dopamine receptors or presence of dopamine receptors in abnormal locations can contribute to aberrant physiological processes, leading to disease, degeneration and other abnormal conditions. Accordingly, the amount or distribution of dopamine receptors in a cell, tissue or organ of an individual can be indicative of a variety of neurological disorders, including central nervous system and peripheral nervous system disorders.

Positron emission tomography (PET) is a high resolution, non-invasive imaging technique that utilizes molecules labeled with positron-emitting radioisotopes to visualize and measure rates of biochemical processes in tissues and cells of living subjects. Single-photon emission computed tomography (SPECT) is another radioisotope imaging modality with similar applications. Both are used in medical imaging of patients for diagnosing disease and monitoring treatment. Imaging of this type is typically done with non-specific compounds complexed with an appropriate positron emitting radionuclide. For example, the most commonly used radiotracer is $^{18}F$ labeled 2-fluoro-2-deoxy-D-glucose (FDG) which is naturally absorbed by cells but cannot be metabolized. When administered, FDG accumulates in cells with a high metabolic rate, a fundamental characteristic of cancer cells. Though PET and SPECT are widely used, few specific radiotracers are readily available as for study of particular biological molecules relevant in medical conditions, such as dopamine receptors.

Owing to the importance of dopamine signaling in neuronal function, considerable effort has been devoted to developing imaging compounds specific for dopamine receptors. (R)-(−)-2-fluoro-N-propylnorapomorphine (1) is recognized as one of the most efficient and most selective $D_2$ dopamine receptor agonists. Considerable effort has previously been devoted to the development of imaging compounds based on apomorphine derivatives (2-23). However, because of the strong ring activation, ring modification is strongly favored in the 2 position of the A ring. Amine, halogen and hydroxyl groups have been placed at this position with an N-n-propyl group and the molecule being otherwise unmodified. An exception to modification of the apomorphine at the 2 position is dibromination at the 8 and 9 positions of the D apomorphine ring (2). In light of the recent appreciation that apomorphine structure around the 1, 2 and 3 positions of the A apomorphine ring has significant effects on the specifics of dopamine receptor interaction, it would be of considerable value to develop a synthetic approach in compounds with a variety of substituents not only at the 1, 2 and 3 positions of the A ring, but also the 8 and 9 positions of the D ring. Thus, there exists a need for apomorphine-based imaging compounds and chemistries for the formation of such compounds so as to enhance neuronal function diagnosis.

SUMMARY OF THE INVENTION

A compound is described having the structural formula:

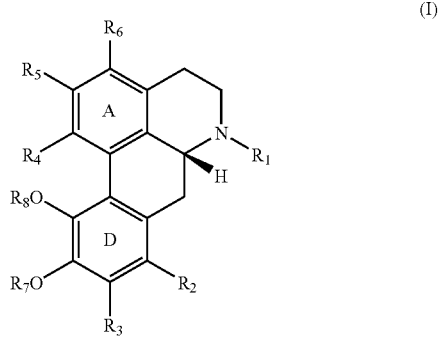

(I)

where $R_1$ is H, $C_1$-$C_{30}$ alkyl, $C_1$-$C_{30}$ alkyl having a substituent of $C_6$-$C_{18}$ aryl, or a heteroatom containing group where the heteroatom is oxygen, nitrogen, or sulfur; $R_2$ is H, X, or $Sn(C_1$-$C_6$ alkyl$)_3$; X is F, Cl, Br, or I; $R_3$ is H, X or $Sn(C_1$-$C_6$ alkyl$)_3$; $R_4$, $R_5$ and $R_6$ are each independently H, nitro, amino, hydroxyl, X, or $C_1$-$C_{30}$ alkyl having a substituent of $C_6$-$C_{18}$ aryl, or a heteroatom containing group where the heteroatom is oxygen, nitrogen, or sulfur; or $Sn(C_1$-$C_6$ alkyl$)_3$ with the proviso that at least one of $R_4$, $R_5$ and $R_6$ is nitro, amino, hydroxyl, X or $Sn(C_1$-$C_6$ alkyl$)_3$; and when $R_5$ is $NH_2$, OH or X; $R_4$ is H; and $R_6$ is H; then at least one of $R_2$ and $R_3$ is X; $R_7$ and $R_8$ are each independently H, $C_1$-$C_6$ alkyl group, or a $C_0$-$C_6$ alkyl group having a substituent of $C_6$-$C_{18}$ aryl, or a heteroatom containing group where the heteroatom is oxygen, nitrogen, or sulfur; where $R_7$ and $R_8$ are optionally fused to form a ring structure, the ring structure optionally having a heteroatom therein and optionally having pendent groups therefrom, the pendent groups each independently selected from H, $C_1$-$C_8$ alkyl, or a $C_0$-$C_8$ alkyl group having a substituent selected from a group consisting of hydroxyl, amine, sulfonate, thiol, carboxyl, substituted amine and quaternary amine.

A process for synthesizing an apomorphine derivative includes reacting a compound having the structural formula

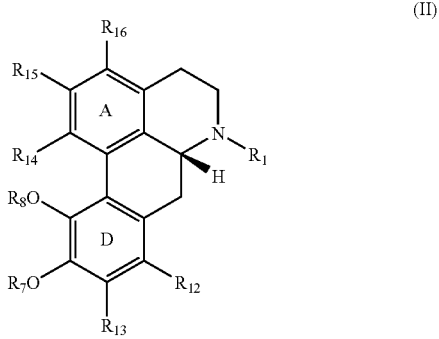

(II)

where $R_1$ is H, $C_1$-$C_{30}$ alkyl, $C_1$-$C_{30}$ alkyl having a substituent of $C_6$-$C_{18}$ aryl, or a heteroatom containing group where the heteroatom is oxygen, nitrogen, or sulfur; $R_2$ and $R_3$ are each H or X and at least one of $R_2$ and $R_3$ is H; X is F, Cl, Br or I; where $R_7$ and $R_8$ are optionally fused to form a ring structure, the ring structure optionally having a heteroatom therein and optionally having pendent groups therefrom, the pendent groups are each independently H, $C_1$-$C_8$ alkyl, or a $C_0$-$C_8$ alkyl group having a substituent selected from a group consisting of hydroxyl, amine, sulfonate, thiol, carboxyl, substituted amine or quaternary amine; $R_{14}$, $R_{15}$, and $R_{16}$ are each independently H, nitro, amino, hydroxyl or X with a halogenating agent imparting a stable halogen isotope to at least one of $R_2$ and $R_3$. Thereafter, at least one of $R_{14}$, $R_{15}$ or $R_{16}$ is replaced with a nitro or X. Alternatively, the stable halogen isotope found at at least one of $R_{12}$ or $R_{13}$ is replaced with a halogen radioisotope. The resulting product is amenable to reduction to convert a nitro group so added to an amine. The amine group is also amenable to hydrolysis to form a hydroxyl group. A nitro group, amine group or hydroxyl group is amenable to direct halogenation of the A ring proximal to the directing group.

A process for detecting dopamine receptor quantity or distribution in an individual or cell, tissue or organ of the individual includes administration of an effective amount of a compound of Formula I to the individual. The compound (I) having a radioisotope at least one of $R_1$-$R_8$. A radioisotopic signal is detected associated with the compound. The signal corresponding to the dopamine receptor quantity or distribution. It is appreciated that introduction of a radioisotopically labeled compound (I) in concert with a drug is operative to assess the receptor kinetics of the drug relative to the compound (I).

A method of diagnosing a neurological disorder includes a comparison of the radioisotopic signal associated with administration of the compound according to Formula I relative to an individual having a control amount or distribution of dopamine receptor and a known neurological state.

The use of a compound having the Formula I is also contemplated for the preparation of a radioimaging composition selective for dopamine receptors. A commercial package is further detailed that includes a compound of Formula I as an active ingredient together with instructions for the use thereof as a radioimaging agent.

DETAILED DESCRIPTION OF THE INVENTION

The present invention has utility as therapeutic targeting dopamine receptors. The radiolabeling of an inventive compound affords a PET or SPECT radioimaging agent specific for detecting dopamine receptors in an individual, an organ, a cellular tissue, or an individual cell.

As used herein "individual" is defined to include a mammalian organism specifically including a human and non-humans including chimpanzees, monkeys, cows, dogs, cats, horses, rabbits, hamsters, rats and mice.

A compound (I) optionally is able to selectively bind to one or more subtypes of dopamine receptors, such as a D1, D2, D3, D4, or D5 dopamine receptor. For example, an apomorphine compound of the invention wherein $R_1$ is methyl or n-propyl can have an ability to bind to a D2 dopamine receptor.

As used herein, the term "selectively" means that the compound binds to one or more particular dopamine receptor subtypes in preference to other dopamine receptor subtypes or unrelated molecules.

It is appreciated that a compound (I) also functions as a dopamine receptor agonist or antagonist. A dopamine receptor agonist refers to a molecule that selectively activates or increases normal signal transduction through the dopamine receptor. A dopamine receptor antagonist refers to a compound that selectively inhibits or decreases normal signal transduction through the dopamine receptor. For diagnostic applications, a dopamine receptor agonist of the invention preferably has an $EC_{50}$, and a dopamine receptor antagonist of the invention preferably has an $IC_{50}$, of less than about $10^{-7}$ M, such as less than $10^{-8}$ M, and more preferably less than $10^{-9}$ M. However, depending on the stability, selectivity and toxicity of the compound, a dopamine receptor agonist with a higher $EC_{50}$, or a dopamine receptor antagonist with a higher $IC_{50}$, can also be useful diagnostically.

A compound of the invention that contains a radioisotopic label can be used in a variety of experimental and diagnostic applications for visualizing dopamine receptors present on a cell, including a subcellular location; a tissue; an organ, or an organism. Such applications include both in vitro and in vivo methods. As an example of an in vitro application, a radioisotopically labeled compound of the invention can be contacted with cultured neurons to assess binding of a dopamine receptor ligand to dopamine receptor-expressing neurons. As an example of an in vivo application, a radioisotopically labeled compound of the invention can be administered to an individual in order to assess the distribution of dopamine receptor-expressing neurons in a tissue. Other exemplary in vivo applications include assessing the level of dopamine receptor-expressing neurons in a particular tissue or organ; assessing occupancy of dopamine receptors in a particular tissue or organ, for example, in the presence of another drug; assessing subcellular localization of dopamine receptors; and assessing the distribution of dopamine receptors or dopamine receptor-expressing neurons in a particular tissue, organ or organism. Such assessments can be used for revealing suitability of a particular therapeutic drug based on dopamine receptor amount or distribution; for providing parameters for optimizing therapeutic effects or minimizing side effects; for validating animal models for human conditions; for determining species differences, and for comparing functional effects of various drugs.

The invention provides a compound having a chemical structure as follows:

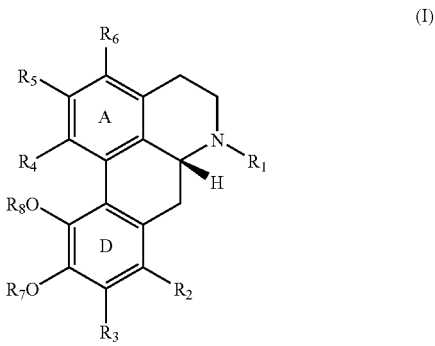

where $R_1$ is H, $C_1$-$C_{30}$ alkyl, or $C_1$-$C_{30}$ alkyl having a substituent of $C_6$-$C_{18}$ aryl, or a heteroatom containing group where the heteroatom is oxygen. nitrogen, or sulfur; $R_2$ is H, X, or Sn($C_1$-$C_6$ alkyl)$_3$; X is F, Cl, Br, or I; $R_3$ is H, X or Sn($C_1$-$C_6$ alkyl)$_3$; $R_4$, $R_5$ and $R_6$ are each independently H, nitro, amino, hydroxyl, X, $C_1$-$C_{30}$ alkyl having a substituent of $C_6$-$C_{18}$ aryl, or a heteroatom containing group where the heteroatom is oxygen, nitrogen, or sulfur; or Sn($C_1$-$C_6$ alkyl)$_3$ with the proviso that at least one of $R_4$, $R_5$ and $R_6$ is nitro, amino, hydroxyl, X or Sn($C_1$-$C_6$ alkyl)$_3$; and when $R_5$ is $NH_2$, OH or X; $R_4$ is H; and $R_6$ is H; then at least one of $R_2$ and $R_3$ is X; $R_7$ and $R_6$ are each independently H, $C_1$-$C_6$ alkyl group, or a $C_0$-$C_6$ alkyl group having a substituent of $C_6$-$C_{18}$ aryl, or a heteroatom containing group where the heteroatom is oxygen, nitrogen, or sulfur; where $R_7$ and $R_8$ are optionally fused to form a ring structure, the ring structure optionally having a heteroatom therein and optionally having pendent groups therefrom, the pendent groups are each independently H, $C_1$-$C_8$ alkyl, or a $C_0$-$C_8$ alkyl group having a substituent of hydroxyl, amine, sulfonate, thiol, carboxyl, substituted amine and quaternary amine.

It is noted that IUPAC positions correspond with variable R groups used herein as follows:

| Variable Group | IUPAC Position |
| --- | --- |
| $R_4$ | 1 |
| $R_5$ | 2 |
| $R_6$ | 3 |
| $R_2$ | 8 |
| $R_3$ | 9 |

Preferably, $R_1$ is a $C_1$-$C_4$ alkyl group. More preferably, $R_1$ is a linear alkyl group. Most preferably, $R_1$ is methyl or n-propyl. It is appreciated that a transport or solubility modifying moiety is readily incorporated into $R_1$. Illustrative modifying moieties include amino acids, dipeptides, sulfonates, amines, and carboxyls. It is appreciated that a radiolabel is also optionally incorporated into $R_1$. Optionally, $R_1$ also includes an unsaturated carbon-carbon bond in the form of an alkenyl, alkynyl or aryl. Heteroatom containing groups operative herein as substituents of $R_1$ illustratively include $(OCH_2CH_2)_n$ or $(OCH_2CH_2CH_2)_n$, where n has a value such that there are thirty or less carbon atoms in the alkyl group of R. Similar compounds having alkyl groups containing a nitrogen or sulfur atom are also encompassed by the present invention.

A compound (I) is operative as a radioimaging agent through radioisotope labeling. Considerable modification is possible when a precursor compound has $R_2$ and $R_3$ that are both bromine, both iodine, or mixed with one of $R_2$ or $R_3$ being bromine and the other being iodine. Such a compound (I) is characterized as having a blocked "D ring," and is suitable starting material for preparing an apomorphine compound having a modified "A ring" or modified A and D rings. Alternatively, A and D rings of a compound (I) are made susceptible to labeling with a halogen isotope; an example of such compound has at least one of $R_4$, $R_5$, or $R_6$ being amine or hydroxyl. In a particular compound, $R_4$ and $R_6$ are both amine, both hydroxyl, or mixed with one of $R_4$ and $R_6$ being amine and the other being hydroxyl. In still another preferred compound amenable to both A and D ring labeling, at least one of $R_4$, $R_5$, or $R_6$ is amine or hydroxyl.

In other embodiments, at least one of $R_4$, $R_5$, or $R_6$ is X. As an example, both $R_4$ and $R_6$ are X in a specific compound. The X is selected from fluorine, chlorine, bromine and iodine. Optionally the halogen is a radioisotope. Halogen isotopes operative herein include $^{18}F$, $^{75}Br$, $^{76}Br$, $^{77}Br$, $^{78}Br$, $^{121}I$, $^{122}I$, $^{123}I$, $^{124}I$, $^{126}I$ and $^{128}I$. Selection of a particular radioisotope for inclusion in a compound of the invention can depend, for example, on the specifics of the PET or SPECT used to detect or monitor the compound in vivo or in vitro.

In further embodiments, $R_2$ and $R_3$ are each independently halogens. For example, $R_2$ and $R_3$ can be each independently bromine or iodine, including compounds where $R_2$ and $R_3$ are both bromine, and where $R_2$ and $R_3$ are iodine. In a particular compound, $R_2$ and $R_3$ are both hydrogen. Additionally, it is appreciated that one of $R_2$ or $R_3$ is readily X while the other is hydrogen.

An inventive compound (I) can be a radiolabeled apomorphine compound containing a detectable moiety, such as a radioisotope. Specific examples of such compounds include those having halogen isotopes at $R_2$, $R_3$, and $R_4$; $R_2$, $R_3$ and $R_5$; $R_2$, $R_3$ and $R_6$; and $R_2$, $R_3$, $R_4$ and $R_6$.

The invention illustratively includes the following compounds. It is appreciated that each instance of $^{18}F$ in each of the following compounds is readily replaced with another halogen. Exemplary specific inventive compounds illustratively include: (R)-(−)-1-Amino-2,8,9-tri[$^{18}F$]fluoroapomorphine; (R)-(−)-2-Amino-1,8,9-tri[$^{18}F$]fluoroapomorphine; (R)-(−)-2-Amino-3,8,9-tri[$^{18}F$]fluoroapomorphine; (R)-(−)-2-Amino-1,3,8,9-tetra[$^{18}F$]fluoroapomorphine; (R)-(−)-3-Amino-2,8,9-tri[$^{18}F$]fluoroapomorphine; (R)-(−)-1-Amino-2,8-di[$^{18}F$]fluoroapomorphine; (R)-(−)-2-Amino-1,8-di[$^{18}F$]fluoroapomorphine; (R)-(−)-2-Amino-3,8-di[$^{18}F$]fluoroapomorphine; (R)-(−)-2-Amino-1,3,8-tri[$^{18}F$]fluoroapomorphine; (R)-(−)-3-Amino-2,8-di[$^{18}F$]fluoroapomorphine; (R)-(−)-1-Amino-2,9-di[$^{18}F$]fluoroapomorphine; (R)-(−)-2-Amino-1,9-di[$^{18}F$]fluoroapomorphine; (R)-(−)-2-Amino-3,9-di[$^{18}F$]fluoroapomorphine; (R)-(−)-2-Amino-1,3,9-tri[$^{18}F$]fluoroapomorphine; (R)-(−)-3-Amino-2,9-di[$^{18}F$]fluoroapomorphine; (R)-(−)-1-Hydroxy-2,8,9-tri[$^{18}F$]fluoroapomorphine; (R)-(−)-2-Hydroxy-1,8,9-tri[$^{18}F$]fluoroapomorphine; (R)-(−)-2-Hydroxy-3,8,9-tri[$^{18}F$]fluoroapomorphine; (R)-(−)-2-Hydroxy-1,3,8,9-tetra[$^{18}F$]fluoroapomorphine; (R)-(−)-3-Hydroxy-2,8,9-tri[$^{18}F$]fluoroapomorphine; (R)-(−)-1-Hydroxy-2,8-di[$^{18}F$]fluoroapomorphine; (R)-(−)-2-Hydroxy-1,8-di[$^{18}F$]fluoroapomorphine; (R)-(−)-2-Hydroxy-3,8-di[$^{18}F$]fluoroapomorphine; (R)-(−)-2-Hydroxy-1,3,8-tri[$^{18}F$]fluoroapomorphine; (R)-(−)-3-Hydroxy-2,8-di[$^{18}F$]fluoroapomorphine; (R)-(−)-1-Hydroxy-2,9-di[$^{18}F$]fluoroapomorphine; (R)-(−)-2-Hydroxy-1,9-di[$^{18}F$]fluoroapomorphine; (R)-(−)-$^{2}$-Hydroxy-3,9-di[$^{18}F$]fluoroapomorphine; (R)-(−)-2-Hydroxy-1,3,9-tri[$^{18}F$]fluoroapomorphine; (R)-(−)-3-Hydroxy-2,9-di[$^{18}F$]fluoroapomorphine; (R)-(−)-1-Amino-2,8,9-tri[$^{18}F$]fluoro-N-n-propylnorapomorphine; (R)-(−)-2-Amino-1,8,9-tri[$^{18}F$]fluoro-N-n-propylnorapomorphine; (R)-(−)-2-Amino-3,8,9-tri[$^{18}F$]fluoro-N-n-propylnorapomorphine; (R)-(−)-$^{2}$-Amino-1,3,8,9-tetra[$^{18}F$]fluoro-N-n-propylnorapomorphine; (R)-(−)-3-Amino-2,8,9-tri[$^{18}F$]fluoro-N-n-propylnorapomorphine; (R)-(−)-1-Amino-2,8-di[$^{18}F$]fluoro-N-n-propylnorapomorphine; (R)-(−)-2-Amino-1,8-di[$^{18}F$]fluoro-N-n-propylnorapomorphine; (R)-(−)-2-Amino-3,8-di[$^{18}F$]fluoro-N-n-propylnorapomorphine; (R)-(−)-2-Amino-1,3,8-tri[$^{18}F$]fluoro-N-n-propylnorapomorphine; (R)-(−)-3-Amino-2,8-di[$^{18}F$]fluoro-N-n-propylnorapomorphine; (R)-(−)-1-Amino-2,9-di[$^{18}F$]fluoro-N-n-propylnorapomorphine; (R)-(−)-2-Amino-1,9-di[$^{18}F$]fluoro-N-n-propylnorapomorphine; (R)-(−)-2-Amino- 3,9-di[$^{18}$F]fluoro-N-n-propylnorapomorphine; (R)-(−)-2-Amino-1,3,9-tri[$^{18}$F]fluoro-N-n-propylnorapomorphine; (R)-(−)-3-Amino-2,9-di[$^{18}$F]fluoro-N-n-propylnorapomorphine; (R)-(−)-1-Hydroxy-2,8,9-tri[$^{18}$F]fluoro-N-n-propylnorapomorphine; (R)-(−)-2-Hydroxy-1,8,9-tri[$^{18}$F]fluoro-N-n-propylnorapomorphine; (R)-(−)-2-Hydroxy-3,8,9-tri[$^{18}$F]fluoro-N-n-propylnorapomorphine; (R)-(−)-2-Hydroxy-1,3,8,9-tetra[$^{18}$F]fluoro-N-n-propylnorapomorphine; (R)-(−)-3-Hydroxy-2,8,9-tri[$^{18}$F]fluoro-N-n-propylnorapomorphine; (R)-(−)-1-Hydroxy-2,8-di[$^{18}$F]fluoro-N-n-propylnorapomorphine; (R)-(−)-2-Hydroxy-1,8-di[$^{18}$F]fluoro-N-n-propylnorapomorphine; (R)-(−)-2-Hydroxy-3,8-di[$^{18}$F]fluoro-N-n-propylnorapomorphine; (R)-(−)-2-Hydroxy-1,3,8-tri[$^{18}$F]fluoro-N-n-propylnorapomorphine; (R)-(−)-3-Hydroxy-2,8-di[$^{18}$F]fluoro-N-n-propylnorapomorphine; (R)-(−)-1-Hydroxy-2,9-di[$^{18}$F]fluoro-N-n-propylnorapomorphine; (R)-(−)-2-Hydroxy-1,9-di[$^{18}$F]fluoro-N-n-propylnorapomorphine; (R)-(−)-2-Hydroxy-3,9-di[$^{18}$F]fluoro-N-n-propylnorapomorphine; (R)-(−)-2-Hydroxy-1,3,9-tri[$^{18}$F]fluoro-N-n-propylnorapomorphine; (R)-(−)-3-Hydroxy-2,9-di[$^{18}$F]fluoro-N-n-propylnorapomorphine; ((R)-(−)-1-Aminoapomorphine; (R)-(−)-3-Aminoapomorphine; (R)-(−)-1,3-Diaminoapomorphine; (R)-(−)-1-Hydroxyapomorphine; (R)-(−)-3-Hydroxyapomorphine; (R)-(−)-1,3-Diydroxyapomorphine; (R)-(−)-1-Amino-N-n-propylnorapomorphine; (R)-(−)-3-Amino-N-n-propylnorapomorphine; (R)-(−)-1,3-Diamino-N-n-propylnorapomorphine; (R)-(−)-1-Hydroxy-N-n-propylnorapomorphine; (R)-(−)-3-Hydroxy-N-n-propylnorapomorphine; (R)-(−)-1,3-Dihydroxy-N-n-propylnorapomorphine.

The present invention provides a method for detecting dopamine receptors in a cell, tissue, organ or body of an individual. The process involves (a) administering an effective amount of a compound of the invention to the individual, where the compound is radioisotopically labeled in at least one of $R_1$-$R_8$, and (b) detecting radioisotopic signal associated with the compound, wherein the signal corresponds to a dopamine receptor amount or distribution in the individual, or a cell, tissue or organ of the individual. It is appreciated that a signal is collected at regular intervals after administration to measure the kinetics of dopamine receptor association by an inventive compound (I) or alternatively, collected after a single time known to provide suitable receptor association.

A radioisotopically labeled compound (I) is also operative to determine how an unlabeled drug affects selective dopamine receptor binding in a cell, tissue or organ by indicating how dopamine receptor occupancy is modified by the drug. An advantage of this approach is that dopamine receptor binding of a drug candidate is determined when the candidate that is not suitable for imaging, for example, due to low binding affinity, lack of selectivity or lack of a chemical structure that facilitates rapid labeling with a radioisotope. Optionally, a clinically relevant dose of such a drug is administered prior to, concurrent with, or subsequent to the compound (I). Screening of a drug candidate or competitive binding of a drug is assessed relative to compound (I) dopamine receptor occupancy in a cell, tissue, organ or body of an individual. The process involves (a) administering an effective amount of a radiolabeled compound (I) and a drug to an individual, tissue, organ or cell, and (b) detecting a radioisotopic signal associated with the compound (I), where the signal corresponds to a dopamine receptor amount or distribution.

The inventive process involves detecting a radioisotopic signal associated with a compound (I). A variety of methods for qualitatively and quantitatively detecting radioisotopes are known in the art and include, for example, imaging methods such as PET or SPECT (24-26).

In an embodiment, a compound of the invention can bind selectively to one or more dopamine receptor subtypes. To determine whether a drug of interest binds to a dopamine receptor subtype to which a particular compound of the invention binds, a variety of competition assays can be performed. Well known formats for competitive ligand binding assays for drug-ligand interactions include pretreatment and displacement assays, both of which are readily performed using imaging methods such as PET or SPECT.

A pretreatment assay involves determining radioisotopic signals associated with the radioisotopically labeled compound in the absence and presence of drug. If dopamine receptors are blocked by a drug administered prior to administration of the radioisotopically labeled compound, the compound cannot bind to the receptors, resulting in a radioisotopic signal that is reduced or ameliorated compared to the baseline signal.

A displacement assay involves determining a baseline radioisotopic signal associated with a radioisotopically labeled compound, and then adding a relatively large amount of unlabeled drug to the dopamine receptors. If the administered drug binds to the same receptors, the radioisotopically labeled compound is displaced, at least in part, from dopamine receptors due to competition for dopamine receptor binding sites. An inventive displacement assay process for detecting dopamine receptors involves administering a compound (I) prior to administration of a drug. An inventive pretreatment assay process for detecting dopamine receptors involves administering a compound (I) after administration of a drug.

The present invention provides a method for diagnosing a neurological disorder. The invention involves (a) administering an effective amount of a compound (I) to an individual having or suspected of having a neurological disorder, wherein the compound is radioisotopically labeled on at least one of $R_1$-$R_8$; (b) detecting a radioisotopic signal associated with the compound (I), where the signal corresponds to a dopamine receptor amount or distribution, and (c) comparing the amount or distribution of dopamine receptor present with a control signal for a known neurological state.

A disorder that can be diagnosed using a method of the invention is one in which the amount or distribution of dopamine receptors correlates with the presence or absence of the disorder. A variety of physiological systems involve dopamine receptor activity that can affect neurological and non-neurological functions of an individual. Exemplary central nervous system disorders involving dopamine receptor activity include schizophrenia, depression, Parkinson's disease, Huntington's chorea, Alzheimer's disease, tardive dyskinesia, phobia disorder, addiction, anxiety disorder, epilepsy, attention deficit disorder and obsessive-compulsive disorder. Exemplary peripheral nervous system disorders involving dopamine receptor activity include gastric and duodenal ulceration and disorders of gastrointestinal motility, gastric mucosal blood flow and gastric acid secretion, and erectile dysfunction. These and other dopamine receptor-related disorders are well known to those skilled in the art. Therefore, the skilled clinician will be able to select an individual appropriate for receiving a diagnostic or prognostic method of the invention.

The invention provides a method for determining a course of treatment for an individual having a neurological disorder. The method involves (a) administering an effective amount of a compound (I) to an individual undergoing medical treatment for the neurological disorder, wherein the compound (I) is radioisotopically labeled on at least one of $R_1$-$R_8$; (b) detecting a radioisotopic signal associated with the compound (I), where the signal corresponds to a dopamine receptor amount or distribution; (c) comparing the amount or distribution of dopamine receptor present in the individual with a control signal indicative of the effectiveness of the medical treatment.

The dosage for an inventive composition is an effective amount of active agent and varies depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired. A typical dosage of active agent is from 1 to 400 milligrams per kilogram of body weight.

Dosage forms suitable for internal administration contain from about 1.0 to about 500 milligrams of active ingredient per unit. In these pharmaceutical compositions, the active ingredient is typically present from 0.05-95% by weight based on the total weight of the dose.

Administration may be by any means suitable for the condition to be treated and may include, for example, oral administration. For example, oral administration is optionally accomplished using solid dosage forms such as capsules, tablets and powders, or in liquid dosage forms such as elixirs, syrups, emulsions and suspensions. The inventive composition is, for example, parenterally administered by injection, rapid infusion, nasopharyngeal adsorption, or dermoabsorption. The inventive composition also is optionally administered intramuscularly, intravenously, intrathecally or as a suppository.

Gelatin capsules may contain inventive composition and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration optionally contain coloring and flavoring to increase patient acceptance.

In general, water, a suitable oil, saline, aqueous dextrose, and related sugar solutions and glycols are suitable carriers for parenteral solutions. Solutions for parenteral administration may contain suitable stabilizing agents and, if necessary, buffer substances. Antioxidizing agents such as sodium bisulfate, sodium sulfite or ascorbic acid either alone or combined are suitable stabilizing agents. Citric acid and its salts and sodium EDTA are also operative herein as stabilizing agents. In addition, parenteral solutions optionally contain preservatives such as benzalkonium chloride, methyl- or propyl-paraben and chlorobutanol. Suitable pharmaceutical carriers are described in Remington's Pharmaceutical Sciences, 20th edition are operative herein.

Additionally, standard pharmaceutical methods can be employed to control the duration of action. These illustratively include control release preparations and can include appropriate macromolecules, for example polymers, polyesters, polyaminoacids, polyvinylpyrrolidone, ethylenevinylacetate, methyl cellulose, carboxymethyl cellulose or protamine sulfate. The concentration of macromolecules as well as the methods of incorporation can be adjusted in order to control release. Additionally, the inventive composition can be incorporated into particles of polymeric materials such as polyesters, polyaminoacids, hydrogels, poly (lactic acid) or ethylenevinylacetate copolymers. In addition to being incorporated, the inventive composition optionally is also used to trap the compound in microcapsules.

Suitable exemplary dosage forms for administration of the inventive composition follow.

Capsules are prepared by filling standard two-piece hard gelatin capsulates each with 100 milligram of powdered active ingredient, 175 milligrams of lactose, 24 milligrams of talc and 6 milligrams magnesium stearate.

A soft gelatin capsule includes mixture of active ingredient in soybean oil is prepared and injected by means of a positive displacement pump into gelatin to form soft gelatin capsules containing 100 milligrams of the active ingredient. The capsules are then washed and dried.

Tablets are prepared by conventional procedures so that the dosage unit is 100 milligrams of active ingredient. 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

A parenteral inventive composition suitable for administration by injection is prepared by stirring 1.5% by weight of active ingredients in 10% by volume propylene glycol and water. The solution is made isotonic with sodium chloride and sterilized.

An aqueous suspension of an inventive composition is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution U.S.P. and 0.025 milligrams of vanillin.

As an encapsulated particulate, active particles of an inventive composition are prepared from a polymer using a coacervation method, with a particle size is between about 5 nm and 750 microns, more preferably between about 10 nm and 500 microns and most preferably between about 50 nm and 800 nm. An inventive composition is complexed to the particles using various methods known to those skilled in the art.

A general method for preparation of such particles is detailed in U.S. Ser. No. 2003/0181367 A1.

The term "effective amount" when used in reference to a compound of the invention means that amount necessary or sufficient to render detectable a cell, tissue or organ that expresses a dopamine receptor. The effective amount varies depending on considerations illustratively including the targeted cell, tissue or organ, the particular compound being administered, the type of individual treated, including considerations of weight, sex, and age. Those skilled in the art can empirically determine the effective amount of a particular compound alone or in conjunction with another agent that allows detection of a selected cell, organ or tissue.

Targeted modification of (R)-(−)-apomorphine
A starting compound has the structural formula

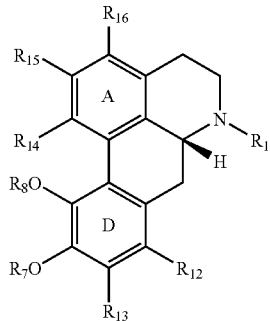
(II)

where $R_1$ is H, $C_1$-$C_{30}$ alkyl, $C_1$-$C_{30}$ alkyl having a substituent selected from the group consisting of: $C_6$-$C_{18}$ aryl, or a heteroatom containing where the heteroatom is oxygen, nitrogen, or sulfur; $R_{12}$ and $R_{13}$ are each H or X and at least one of $R_{12}$ and $R_{13}$ is H; X is F, Cl, Br or I; where $R_7$ and $R_8$ are optionally fused to form a ring structure, the ring structure optionally having a heteroatom therein and optionally having pendent groups therefrom, the pendent groups each independently selected from H, $C_1$-$C_8$ alkyl, and a $C_0$-$C_8$ alkyl group having a substituent selected from a group consisting of hydroxyl, amine, sulfonate, thiol, carboxyl, substituted amine and quaternary amine; $R_{14}$, $R_{15}$, and $R_{16}$ are each independently H, nitro, amino, hydroxyl and X.

A particularly preferred starting compound II has $R_{12}$-$R_{16}$ all being hydrogen and corresponds to (R)-(−)-apomorphine.

The two phenyl rings (A and D) of the general structure II above differ markedly in chemical activation. It has been demonstrated for (R)-(−)-apomorphine ($R_1$=methyl) that the D phenyl ring $R_{12}$ and $R_{13}$ positions can be specifically brominated under mild conditions (2). This exclusive activation allows other similar halogenations including the selective fluorination, bromination and iodination of the D ring $R_{12}$ and/or $R_{13}$ positions of general structure II for any $R_1$ group by standard methods using elemental fluorine, bromine and iodine respectively. The activation of the D ring allows the preparation of PET and SPECT ligands labeled in the $R_{12}$ and/or $R_{13}$ positions with such isotopes as $^{18}F$, $^{76}Br$, $^{123}I$ or $^{124}I$.

$^{18}F$ inventive compounds I are directly labeled in the D ring $R_2$ and/or $R_3$ positions with this isotope using $^{18}F_2$ (27, 28) or by means of $Xe^{18}F_2$ (29). Aromatic bromides (30) and iodides (31) are transformed into aromatic trialkyl tin (stannyl) derivatives via palladium catalysts. As a result a stannyl group or groups replace D ring $R_{12}$ and/or $R_{13}$ of general structure II. Such D ring stannyl derivatives of general structure I represent precursors to D ring $R_2$ and/or $R_3$ position $^{18}F$ analogues of inventive compound I using $^{18}F_2$ (32). Alternatively, $^{18}F$ analogs of general structure I are obtained by $^{18}F$ exchange with stable isotope $^{19}F$, $R_2$ and/or $R_3$ groups (33).

Bromine radiolabeled compound I is directly labeled in the D ring $R_{12}$ or $R_{13}$ positions of structure II (34). Alternatively, the stannyl analogs represent a precursor for $^{76}Br$ introduction at $R_2$ and/or $R_3$ (30). It is appreciated that $^{75}Br$ and $^{77}Br$ are also introduced in this way and likewise operative in PET and SPECT. In principle, these procedures should also be capable of labeling the D ring $R_2$ and/or $R_3$ positions of general structure I with any other useful PET or SPECT isotope of Bromine including $^{75}Br$ and $^{77}Br$.

For $^{123}I$ or $^{124}I$, general structure II is directly labeled in the D ring $R_{12}$ and/or $R_{13}$ positions with either isotope by analogy with the method of DeVos and co-workers (35). Alternatively, utilizing the stannyl analogues of general structure I, $^{123}I$ and $^{124}I$ are introduced into the D ring $R_2$ and/or $R_3$ according to the methods of John and co-workers (36) and Koziorowski and co-workers (37) respectively.

It is appreciated that the use of excess halogenation reagent, more than an equivalent per equivalent per D ring hydrogen of general structures I or II, promotes labeling in both the $R_2$ and $R_3$, and $R_{12}$ and $R_{13}$ positions, respectively. Use of an equivalent or less of halogenation reagent relative to D ring hydrogen produce a mixture of $R_2$ and $R_3$ substituted halogen analogs. All D ring 8 and 9 position mono- and di-substituted halogen analogs so produced are resolved by standard HPLC procedures.

In order to modify the A ring of structure II, the more active D ring is first halogenated as detailed above. With precursor sites $R_{12}$ and $R_{13}$ of structure II blocked with halogens, X, the resulting compound is amenable to direct halogenation with isoptically natural dihalogen gases or isotopically enriched gases to produce a mixture of A ring mono-, di- and tri-halo compounds at $R_4$, $R_5$, and $R_6$ (38). Specifically, addition of $^{18}F$ to the A ring creates compounds well suited as PET and SPECT imaging agents. The resulting compounds are optionally catalytically hydrogenated to preferentially remove the D ring halogens to produce various A ring mono-, di- and tri-halo compounds at $R_4$, $R_5$, and $R_6$ with the substitution pattern in the A ring as any possible combination of A ring positional isomers and lacking a halogen in the D ring. The A ring isotopically-unenriched halogenated compounds of formula I also serve as precursors to the corresponding radioisotope analogues by means of exchange (33). While isotopically enriched analogues of formula I would be valuable as a mixture, resolution from one another is exacted by standard HPLC purification procedures.

Upon halogenating the D ring of general structure I various activated A ring amino, hydroxyl and combinations thereof are formed with such moieties at $R_4$ and/or $R_5$ and/or $R_6$ by means of the following sequence: following the halogenation of $R_{12}$ and $R_{13}$ of structure II, the A ring is directly nitrated (39). The stoichiometry and experimental details of these nitrations are manipulated to provide a mixture of various A ring mono- and di-substituted nitro analogs of structure I with the nitro substitution pattern in the A ring as any possible combination of $R_4$, $R_5$, and $R_6$ positional isomers. Due to the ring deactivating effect of the nitro groups, trinitro substitution on the A ring of these intermediates is rarely observed. The A ring mono- or di-substituted nitro analogs are then selectively reduced with stannous chloride (40) or some other nitroselective reducing reagent to yield various A ring mono- and di-substituted amine analogs with the amine substitution pattern in the A ring as any possible combination of $R_4$, $R_5$, and $R_6$ positional isomers. These mono- and di-substituted amine analogs are optionally converted to the corresponding intermediate A ring mono and di-substituted hydroxyl analogues by nitrosation/hydrolysis (39). In the case of a di-amino or di-hydroxyl compound of structure I, it is appreciated that protecting groups are readily employed to allow for the subsequent reaction of the non-protected group. Selective protection occurs through control of protecting group stoichiometry relative to the number of protectable moieties per compound of structure I. In this way, an A ring having a multiple non-hydrogen moieties is produced. As detailed above, isomers are resolved by standard HPLC purification procedures.

An inventive compound of structure I containing amino and or hydroxyl groups is converted to PET and SPECT radioligands labeled with $^{18}F$ in the unsubstituted positions of the A ring. The amino and/or hydroxyl containing A ring compound is directly labeled in the unsubstituted A ring positions with $^{18}F_2$ (27, 28) or by means of $Xe^{18}F_2$ (29). Alternatively, the amino and/or hydroxyl containing A ring compound is fluorinated in the unsubstituted A ring positions and these fluoro analogs serve as I precursors to $^{18}F$ analogs by $^{18}F$ exchange (33). After $^{18}F$ has been introduced into the A ring, $R_2$ and/or $R_3$ halogens are optionally catalytically hydrogenated to preferentially remove the D ring halogens to produce various A ring amino or hydroxyl $^{18}F$ analogs with any possible combination of $^{18}F$, amine or hydroxyl at $R_4$, $R_5$, and $R_6$ in the A ring positions. It is appreciated that the use of excess fluorination reagent promotes multiple radioisotope ring labeling, while use of an equivalent or less of fluorination reagent tends to produce a mixture of various mono substituted $^{18}F$ analogs. Such mixtures are resolved to pure isomers by appropriate standard HPLC purification procedures.

It is appreciated that repetition of the above nitration, after modifying the A ring represents a method by which a nitro group is added to the D ring at $R_2$ or $R_3$. A subsequent catalytic hydrogenation reaction, as detailed converts the $R_2$ or $R_3$ nitro to an amine group. As detailed above, the amine is optionally converted to a hydroxyl group. A hydrogen remaining at $R_2$ or $R_3$ is optionally halogenated with an isotopically unenriched or radioisotope to re-insert a halogen on the D ring.

A protecting group for a hydroxyl function also may prove useful in the practice of the present invention. Examples of hydroxyl protecting groups illustratively include tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4''-trimethoxytrityl, benzyl, allyl, trimethylsilyl, (t-butyl)dimethylsilyl, 2,2,2-trichloroethoxycarbonyl, and the like.

Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3. A preferred hydroxy-protecting group is the tert-butyl group.

A protecting group for the amino function can be an acyl group, such as an acyl of an aliphatic, aromatic or araliphatic carboxylic acid, especially lower alkanoyl such as acetyl or propionyl, or aryl such as benzoyl, or formyl or an acyl of a carbonic acid half-ester, such as benzyloxycarbonyl or fluorenylmethyloxycarbonyl (Fmoc). Examples of amino-protecting groups illustratively include the formyl ("For") group, the trityl group, the phthalimido group, the trichloroacetyl group, the trifluoroacetyl group, the chloroacetyl, bromoacetyl, and iodoacetyl groups, urethane-type protecting groups, such as t-butoxycarbonyl ("t-Boc"), 2-(4-biphenylyl)propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxycarbonyl, 1-methyl-cyclohexanyloxycarbonyl, 2-methylcyclohexanyl-oxycarbonyl, 2-(4-toluylsulfonyl)ethoxycarbonyl, 2-(methylsulfonyl)ethoxycarbonyl, 2-(triphenylphosphino)-ethoxycarbonyl, 9-fluorenylmethoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyl-oxycarbonyl, 2,2,2-trichloroethoxycarbonyl, 2-ethynyl-2-propoxycarbonyl, cyclopropylmethoxycarbonyl, isobomyloxycarbonyl, 1-piperidyloxycarbonyl, benzyloxycarbonyl ("Cbz"), 4-phenylbenzyloxycarbonyl, 2-methylbenzyloxycarbonyl, α-2,4,5,-tetramethylbenzyl-oxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl and the like; the benzoylmethylsulfonyl group, the 2,2,5,7,8-pentamethylchroman-6-sulfonyl group ("PMC"), the dithiasuccinoyl ("Dts") group, the 2-(nitro)phenyl-sulfenyl group ("Nps"), the diphenylphosphine oxide group, and like amino-protecting groups. The species of amino-protecting group employed is not critical so long as the derivatized amino group is stable to the conditions of the subsequent reaction(s) and can be removed at the appropriate point without disrupting the remainder of the molecule. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," $2^{nd}$ ed., John Wiley and Sons, New York, N.Y., 1991, Chapter 7; M. Bodanzsky, "Principles of Peptide Synthesis," $1^{st}$ and $2^{nd}$ revised Ed., Springer-Verlag, New York, N.Y., 1984 and 1993; and J. M. Stewart and J. D. Young, "Solid Phase Peptide Synthesis," $2^{nd}$ Ed., Pierce Chemical Co., Rockford, Ill., 1984; E. Atherton and R. C. Shephard, "Solid Phase Peptide Synthesis—A Practical Approach" IRL Press, Oxford, England (1989).

The cleavage of such an acyl residue serving as protecting group for an amino function can be performed by known methods, such as solvolysis exemplified by alcoholysis. Moreover it can be brought about by hydrolysis in acidic or basic medium. The alcoholytic cleavage of an acyl residue can be effected, such as in presence of a basic reagent and/or at elevated temperature, e.g. from 50° C. to 120° C. with a lower alkanol such as n-butanol or ethanol. A base is used such as an alkali metal alcoholate, such as sodium or potassium ethoxide or an alkali metal hydroxide, such as sodium or potassium hydroxide.

Other aminoprotecting groups, such as lower alkoxycarbonyl-groups e.g. t-butoxycarbonyl, are cleaved under mild acidic conditions, such as by treatment with trifluoroacetic acid. Another group, cleavable under especially mild conditions is an ethoxycarbonyl group carrying in the β-position a silyl group substituted with three hydrocarbon residues, such as triphenylsilyl, dimethyl-butylsilyl or especially trimethylsilyl. These are cleaved by reaction with fluoride ions, especially fluoride salts of quaternary ammonium bases, such as tetraethylammonium fluoride.

In order to more fully demonstrate the advantages arising from the present invention, the following examples are set forth. It is to be understood that the following is by way of example only and not intended as a limitation on the scope of the invention.

EXAMPLE 1

(R)-(−)-8,9-dibromoapomorohine hydroiodide precursor

The title compound is prepared according to Filer et al. (2). The synthesis included dissolution of 100 milligrams of (R)-(−)-apomorphine hydrochloride in 30 milliliters of trifluoroacetic acid. 30 microliters of bromine in 7 milliliters of trifluoroacetic acid, representing 2 mols of bromine per mol of (R)-(−)-apomorphine, is added dropwise over 20 minutes at room temperature to yield a crystalline precipitate. Filtering and washing with cold trifluoroacetic acid yielded an off-white solid corresponding to the title compound.

EXAMPLE 2

(R)-(−)-8,9-diiodoapomorphine precursor

The procedure of Example 1 is repeated except an equivalent stoichiometric amount of iodine is substituted for bromine. A solid product corresponding to the title compound is obtained.

EXAMPLE 3

(R)-(−)-8,9-difluoroapomorphine precursor 0.68 millimoles of xenon difluoride was added to 0.33 millimoles of (R)-(−)-apomorphine hydrochloride in 50 ml of dichloromethane. The solution is heated to 40° Celsius for one hour to yield the title compound.

EXAMPLE 4

(R)-(−)-8,9-di(trimethylstannyl) apomorphine

The dibromoapomorphine produced in Example 1 is refluxed with a stoichiometric amount of hexamethyl ditin and tetrakis (triphenylphosphine) palladium in dioxane to obtain the title compound in about 50% yield.

EXAMPLE 5

(R)-(−)-8,9-di[$^{18}$F]fluoroapomorphine

The compound having trimethyl tin at the 8 and 9 positions of (R)-(−)-apomorphine produced according to Example 4 is introduced into 5 milliliters of chloroform in an amount of 100 micromoles. 0.5 milliliters of concentrated HCl is added. [$^{18}$F]F$_2$ is bubbled into the reaction mixture with stirring for 10 minutes. The reaction is quenched with sodium sulfite and loaded onto a C-18 SEP-pack, washed with water and eluted with ethanol further purified by HPLC (30). The title compound was obtained with a radiochemical yield of 40%.

EXAMPLE 6

Synthesis of mono-, di- and tri-fluoro-8,9-dibromoapomorphines 200 micromoles of a dibromoapomorphine as produced in Example 1 is dissolved in 10 milliliters of trifluoroacetic acid through which fluorine is bubbled at room temperature for 20 minutes. The resulting reaction mixture is resolved with HPLC (30) to obtain the (R)-(−)-1,2,3-trifluoro-8,9 dibromoapomorphine; (R)-(−)-2-fluoro-8,9 dibromoapomorphine; and 3 isomers of (R)-(−)-difluoro-8,9 dibromoapomorphine.

EXAMPLE 7

Synthesis of (R)-(−)-1,2,3 trifluoroapomorphine

The trifluoro dibromoapomorphine produced according to Example 6 is reduced with hydrogen in 10 milliliters of ethanol using 30 milligrams of 10% palladium/carbon at room temperature in the dark for 2 hours with stirring (2) to yield the title compound.

EXAMPLE 8

Synthesis of (R)-(−)-1,3 dinitro-8,9 dibromo apomorphine (R)-(−)-8,9-dibromo apomorphine as made in Example 1 is dissolved in 30 milliliters of sulfuric acid with cooling. 20 milliliters of concentrated nitric acid is added dropwise with stirring to maintain the temperature below 5° Celsius. The reaction mixture is stirred at room temperature for 16 hours and poured onto ice. The resulting solution is neutralized with aqueous ammonia and extracted with chloroform. The chloroform extract is dried over sodium sulfate and evaporated under vacuum to yield a mixture of nitrated apomorphines.

EXAMPLE 9

Synthesis of (R)-(−)-1,3-diamino apomorphine

The product obtained from the procedure of Example 8 is dissolved in approximately 200 milliliters ethanol and subjected to catalytic hydrogenation at 60 pounds per square inch in room temperature for 20 hours in the presence of 10% palladium on charcoal (1 gram). The resulting solution is filtered and evaporated under vacuum to yield the title compound.

EXAMPLE 10

Synthesis of (R)-(−)-1-amino-3-hydroxy-8,9-dibromoapomorphine 20 micromoles of (R)-(−)-1,3-diamino 8,9-dibromoapomorphine is reacted with an equivalent amount of fluorenylmethyloxycarbonyl chloride in the presence of 60 micromols of pyridine in dichloromethane at room temperature for 1 hour. A mix of protected groups on the 1 and 3 positions of apomorphine is noted. The resulting partially protected apomorphine is dissolved in a mixture of concentrated sulfuric acid (10 ml) and ice (30 grams). An aqueous solution of sodium nitrite is added dropwise over 30 minutes while the temperature is maintained about 0° Celsius for 8 hours. Urea is added thereafter and filtered. The solution is slowly added to 200 milliliters of 2 molar sulfuric acid and thereafter cooled and extracted with chloroform. The extract is washed with 10% sodium hydroxide to yield a mixture of (R)-(−)-1-amino-3-hydroxy-8,9 dibromoapomorphine and (R)-(−)-1-hydroxy-3-amino-8,9 dibromoapomorphine.

EXAMPLE 11

Synthesis of (R)-(−)-1-amino-2-[$^{85}$Br]bromo-3-hydroxyl-8,9 difluoroapomorphine 10 micromols of (R)-(−)-1-amino-3-hydroxyl-8,9 difluoroapomorphine is reacted with n-butoxycarbonyl ether in a mixture of dry triethylamine and dimethylformamide at room temperature (41). 1-Boc-3-hydroxyl-8,9 fluoroapomorphine is an intermediate that in turn is reacted with [$^{76}$Br] ammonium bromide in the presence of peracetic acid, acetic acid and a mixture of methanol in water at room temperature to afford the title product after reaction with trifluoroacetic acid to deprotect the 1 position amine.

REFERENCES CITED

1. J. L. Neumeyer et al., Synthesis and dopamine receptor affinity of (R)-(−)2-fluoro-N-n-propylnorapomorphine: A highly potent and selective dopamine D2 agonist, J. Med. Chem. 33, 3122-3124 (1990).
2. C. N. Filer et al., Preparation of (−)-[8,9-$^3$H] apomorphine at high specific activity, J. Org. Chem. 45, 3918-3919 (1980).
3. S. Rambsy et al., 2-Haloaporphines as potent dopamine agonists, J. Med. Chem. 32, 1198-1201 (1989).
4. J. A. Weisbach et al., Studies in the synthesis and pharmacology of aporphines, J. Med. Chem. 6, 91-97 (1963).
5. J. L. Neumeyer et al., Preparation of noraporphine dopamine agonist compounds, PCT Int. Appl. WO 9012574 A1 19901101, WO 1989US1747 19890425.
6. R. J. Baldessarini et al., R(−)-2-Fluoro-N-n-propylnorapomorphine: A very potent and D2-selective dopamine agonist, Neuropharmacol. 30, 97-99 (1991).
7. S. Berenyi et al., A new efficient method for the preparation of 2-fluoro-N-propylnorapomorphine, J. Chem. Soc. Perkin Trans. 1, 2693-2694 (1992).
8. S. Berenyi et al. Process for preparing N-substituted N-demethylated 2-fluoroapocodeine and apomorphine derivatives, Hung. Teljes HU 66556 A2 19941228 APPLICATION: HU 19929201501 19920505.
9. Y. Gao et al., Synthesis and structural requirements of N-substituted norapomorphines for affinity and activity at dopamine D-1, D-2, and agonist receptor sites in rat brain, J. Med. Chem. 33, 39-44 (1990).
10. I. Morin et al., N-Monofluoroalkylnoraporphines: synthesis and binding dopamine receptor studies, Med. Chem. Res. 2, 354-360 (1992).
11. S. Zijlstra et al., Synthesis and in vivo distribution in the rat of several fluorine-18 labeled N-fluoroalkylaporphines, Appl. Radiat. Isot. 44, 651-658 (1993).
12. N. M. Gillings et al., An improved synthesis and evaluation in pig brain of the dopamine agonist ligand: R-[N-methyl-$^{11}$C] apomorphine, J. Labelled Cpd. Radiopharm. 44(Suppl 1), S210-S212 (2001).
13. S. Zijlstra et al., Synthesis and in vivo distribution in the rat of a dopamine agonist: N-([$^{11}$C] methyl)norapomorphine Nucl. Med. Biol. 20, 7-12 (1993).
14. D.-R. Hwang et al., (−)-N-[$^{11}$C] Propyl-norapomorphine: A positron-labeled dopamine agonist for PET imaging of D2 receptors, Nucl. Med. Biol. 27, 533-539 (2000).
15. P. Cumming et al., Kinetics of the uptake and distribution of the dopamine D2,3 agonist (R)-N-[1-$^{11}$C]n-propyl-norapomorphine in brain of healthy and MPTP-treated Gottingen miniature pigs, Nucl. Med. Biol. 30, 547-553 (2003).
16. J.-H. Guan et al., Aporphines 58. N-(2-chloroethyl)[8,9-$^2$H] norapomorphine, an irreversible ligand for doparine receptors: synthesis and application. J. Med. Chem. 27, 806-810 (1984).
17. S. Hosztafi et al., Synthesis of new apomorphine derivatives containing halogen (Cl and Br) in ring-D. Synth. Commun. 26, 3909-3918 (1996).
18. S. Zijlstra et al., Synthesis and In vivo distribution in the rat of a dopamine agonist: N-([$^{11}$C]methyl)norarpomorphine, Nucl. Med. Biol. 20, 7-12 (1993).
19. R. V. Smith et al. Synthesis of 10,11-dimethoxyaporphine-$d_8$. Use of Eu(FOD)$_3$ reagent in structure determination. Tet. Lett. 1819-1822 (1973).
20. D.-R. Hwang et al. Characterization of dopamine agonist PET tracer: $^{11}$C-NPA. J. of Nucl. Med. (Suppl. 5) 235 (2002).
21. R. Narendran et al., In vivo vulnerability to competition by endogenous dopamine: Comparison of the D2 receptor agonist radiotracer (−)-N-[$^{11}$C] propyl-norapomorphine ([$^{11}$C] NPA) with the D2 receptor antagonist radiotracer [$^{11}$C]-raclopride. Synapse 52(3), 188-208 (2004).
22. D.-R. Hwang et al., Positron-labeled dopamine (DA) agonist for probing the high affinity states of DA receptors. Abs. of Papers, 227$^{th}$ ACS Natl. Meeting, Anaheim, Calif.; Mar. 28-Apr. 1, 2004.
23. D.-R. Hwang et al., Quantitative analysis of (−)-N-$^{11}$C-propyl-norapomorphine in vivo binding in non-human primates. J. of Nucl. Med. 45(2), 338-346 (2004).
24. Von Schulthess et al., Clinical Molecular Anatomic Imaging (Lippincott Williams & Wilkins, 2003).
25. Maisey et al., Atlas of Clinical Positron Emission Tomography (London, 1999).
26. Seeram et al., Computed Tomography: Physical Principles, Clinical Applications, and Quality Control (W B Saunders, 2001).
27. N. Vasdev et al. J. Labelled Cpd. Radiopharm. 44 (Suppl. 1), S863-S865 (2001).
28. N. Vasdev et al. J. Labelled Cpd. Radiopharm. 42 (Suppl. 1), S486-S488 (1999).
29. M. Constantinou et al. J. Labelled Cpd. Radiopharm. 42 (Suppl. 1), S530-S532 (1999).
30. C. Loc'h et al. J. Labelled Cpd. Radiopharm. 42 (Suppl. 1), S42-S44 (1999).
31. G. A. Pacer et al. J. Labelled Cpd. Radiopharm. 44 (Suppl. 1), S920-S921 (2001).
32. F. Fuchtner et al. J. Labelled Cpd. Radiopharm. 42 (Suppl. 1), S267-S269 (1999).
33. T. Tierling et al. J. Labelled Cpd. Radiopharm. 44 (Suppl. 1), S146-S147.
34. O. Langer et al. J. Labelled Cpd. Radiopharm. 40, 117-119 (1997).
35. F. DeVos et al. J. Labelled Cpd. Radiopharm. 40, 375-376 (1997).
36. C. S. John et al. J. Labelled Cpd. Radiopharm. 42 (Suppl. 1), S261-S263 (1999).
37. J. Koziorowski et al. J. Labelled Cpd. Radiopharm. 40, 128 (1997).
38. J. A. Cramer et al. J. Amer. Chem. Soc. 96, 6579-6584 (1974).
39. J. F. Ajao et al. J. Heterocyclic Chem. 22, 329-331 (1985).
40. C. N. Filer et al. J. Org. Chem. 43, 672-675 (1978).
41. S. G. Mislankar et al. J. Med. Chem. 31, 362-366 (1988).

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

Although specific embodiments have been illustrated and described herein, it will be appreciated by those skilled in the art that any arrangement which is determined to achieve the same purpose may be substituted for the specific embodiments shown. This application is intended to cover any adaptations or variations of the present invention.

The invention claimed is:

1. A compound having the structural formula:

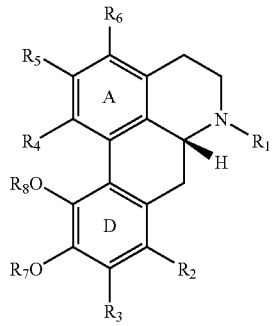

(I)

where $R_1$ is H, $C_1$-$C_{30}$ alkyl, or $C_1$-$C_{30}$ alkyl having a substituent of $C_6$-$C_{18}$ aryl, or a heteroatom containing group where the heteroatom is oxygen, nitrogen, or sulfur; $R_2$ is H, X, or $Sn(C_1$-$C_6$ alkyl$)_3$; X is F, Cl, Br, or I; $R_3$ is H, X or $Sn(C_1$-$C_6$ alkyl$)_3$; $R_4$, $R_5$ and $R_6$ are each independently H, nitro, amino, hydroxyl, X, or $C_1$-$C_{30}$ alkyl having a substituent of $C_6$-$C_{18}$ aryl; or $Sn(C_1$-$C_6$ alkyl$)_3$ with the proviso that at least one of $R_4$, $R_5$ and $R_6$ is nitro, amino, hydroxyl, X or $Sn(C_1$-$C_6$ alkyl$)_3$; and when $R_5$ is $NH_2$, OH or X; $R_4$ is H; and $R_6$ is H; then at least one of $R_2$ and $R_3$ is X; $R_7$ and $R_8$ are each independently H, $C_1$-$C_6$ alkyl group, a $C_1$-$C_6$ alkyl group having a substituent of $C_6$-$C_{18}$ aryl; where $R_7$ and $R_8$ are optionally fused to form a ring structure, the ring structure optionally having a heteroatom therein and optionally having pendent groups therefrom, the pendent groups each independently selected from H, $C_1$-$C_8$ alkyl, or a $C_1$-$C_8$ alkyl group having a substituent of hydroxyl, amine, sulfonate, thiol, carboxyl, substituted amine or quaternary amine; wherein at least one of $R_2$-$R_6$ is X and wherein X in at least one occurrence is a radioisotope.

2. The compound of claim 1, wherein at least one of $R_4$, $R_5$, or $R_6$ is amine or hydroxyl.

3. A compound having the structural formula:

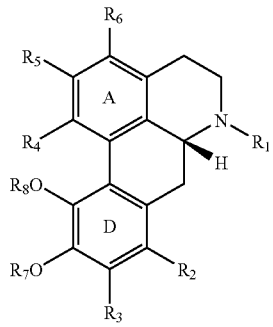

(I)

where $R_1$ is, $C_1$-$C_{30}$ alkyl, or $C_1$-$C_{30}$ alkyl having a substituent of $C_6$-$C_{18}$ aryl, or a heteroatom containing group where the heteroatom is oxygen, nitrogen, or sulfur; $R_2$ is H, X, or $Sn(C_1$-$C_6$ alkyl$)_3$; X is F, Cl, Br, or I; $R_3$ is H, X or $Sn(C_1$-$C_6$ alkyl$)_3$; $R_4$ and $R_6$ are both amine or hydroxyl, $R_5$ is H, nitro, amino, hydroxyl, X, or $C_1$-$C_{30}$ alkyl having a substituent of $C_6$-$C_{18}$ aryl or $Sn(C_1$-$C_6$ alkyl$)_3$; $R_7$ and $R_8$ are each independently H, $C_1$-$C_6$ alkyl group, a $C_1$-$C_6$ alkyl group having a substituent of $C_6$-$C_{18}$ aryl; where $R_7$ and $R_8$ are optionally fused to form a ring structure, the ring structure optionally having a heteroatom therein and optionally having pendent groups therefrom, the pendent groups each independently selected from H, $C_1$-$C_8$ alkyl, or a $C_1$-$C_8$ alkyl group having a substituent of hydroxyl, amine, sulfonate, thiol, carboxyl, substituted amine or quaternary amine.

4. The compound of claim 1, wherein at least one of $R_4$, $R_5$, or $R_6$ is X.

5. A compound having the structural formula:

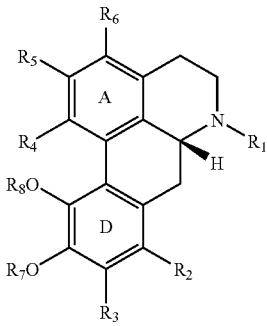

(I)

where $R_1$ is H, $C_1$-$C_{30}$ alkyl, or $C_1$-$C_{30}$ alkyl having a substituent of $C_6$-$C_{18}$ aryl, or a heteroatom containing group where the heteroatom is oxygen, nitrogen, or sulfur; $R_2$ is H, X, or $Sn(C_1$-$C_6$ alkyl$)_3$; X is F, Cl, Br, or I; $R_3$ is H, X or $Sn(C_1$-$C_6$ alkyl$)_3$; both $R_4$ and $R_6$ are X; $R_5$ is nitro, amino, hydroxyl, X or $Sn(C_1$-$C_6$ alkyl$)_3$; $R_7$ and $R_8$ are each independently H, $C_1$-$C_6$ alkyl group, a $C_1$-$C_6$ alkyl group having a substituent of $C_6$-$C_{18}$ aryl; where $R_7$ and $R_8$ are optionally fused to form a ring structure, the ring structure optionally having a heteroatom therein and optionally having pendent groups therefrom, the pendent groups each independently selected from H, $C_1$-$C_8$ alkyl, or a $C_1$-$C_8$ alkyl group having a substituent of hydroxyl, amine, sulfonate, thiol, carboxyl, substituted amine or quaternary amine.

6. The compound of claim 1, wherein X in each occurrence is F.

7. The compound of claim 1, wherein X in each occurrence is $^{18}$F.

8. The compound of claim 1, wherein $R_1$ is methyl.

9. The compound of claim 1, wherein $R_1$ is n-propyl.

10. A compound having the structural formula:

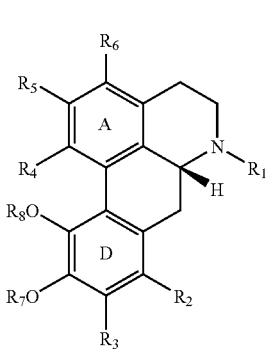

(I)

where $R_1$ is H, $C_1$-$C_{30}$ alkyl, or $C_1$-$C_{30}$ alkyl having a substituent of $C_6$-$C_{18}$ aryl, or a heteroatom containing group where the heteroatom is oxygen, nitrogen, or sulfur; $R_2$ is X; X is F, Cl, Br, or I; $R_3$ is X; $R_4$, $R_5$ and $R_6$ are each independently nitro, amino, hydroxyl, X, or $C_1$-$C_{C30}$ alkyl having a substituent of $C_6$-$C_{18}$ aryl; or $Sn(C_1$-$C_6$ alkyl$)_3$; $R_7$ and $R_8$ are each independently H, $C_1$-$C_6'$ alkyl group, a $C_1$-$C_6$ alkyl group having a substituent of $C_6$-$C_{18}$ aryl; where $R_7$ and $R_8$ are optionally fused to form a ring structure, the ring structure optionally having a heteroatom therein and optionally having pendent groups therefrom, the pendent groups each independently selected from H, $C_1$-$C_8$ alkyl, or a $C_1$-$C_8$ alkyl group having a substituent of hydroxyl, amine, sulfonate, thiol, carboxyl, substituted amine or quaternary amine.

11. The compound of claim 10, wherein $R_2$ and $R_3$ are each independently bromine or iodine.

12. The compound of claim 11, wherein both $R_2$ and $R_3$ are bromine.

13. The compound of claim 11, wherein both $R_2$ and $R_3$ are iodine.

14. The compound of claim 1, wherein both $R_2$ and $R_3$ are hydrogen.

15. The compound of claim 10, wherein X is a radioisotope.

16. The compound of claim 15, wherein X is $^{18}F$.

17. A process of synthesizing an apomorphine derivative comprising:

reacting a compound having the structural formula:

(II)

where $R_1$ is H, $C_1$-$C_{30}$ alkyl, $C_1$-$C_{30}$ alkyl having a substituent of $C_6$-$C_{18}$ aryl, or a heteroatom containing group where the heteroatom is oxygen, nitrogen, or sulfur; $R_{12}$ and $R_{13}$ are each H or X and at least one of $R_{12}$ and $R_{13}$ is H; X is F, Cl, Br or I; $R_7$ and $R_8$ are each independently H, $C_1$-$C_6$ alkyl group, a $C_1$-$C_6$ alkyl group having a substituent of $C_6$-$C_8$ aryl; where $R_7$ and $R_8$ are optionally fused to form a ring structure, the ring structure optionally having a heteroatom therein and optionally having pendent groups therefrom, the pendent groups are each independently H, $C_1$-$C_8$ alkyl, or a $C_1$-$C_8$ alkyl group having a substituent of hydroxyl, amine, sulfonate, thiol, carboxyl, substituted amine or quaternary amine; $R_{14}$, $R_{15}$, and $R_{16}$ are each independently H, nitro, amino, hydroxyl or X;

with a halogenating agent imparting a stable halogen isotope to at least one of $R_{12}$ and $R_{13}$; and replacing at least one of $R_{14}$, $R_{15}$, or $R_{16}$ with a halogen radioisotope.

18. The process of claim 17 wherein $R_{14}$, $R_{15}$, and $R_{16}$ are all hydrogen prior to replacement.

19. The process of claim 17 wherein at least one of $R_{14}$, $R_{15}$, or $R_{16}$ is a nitro group.

20. The process of claim 19 further comprising reducing said nitro group to an amine group.

21. The process of claim 20 further comprising the step of hydrolyzing said amine group to a hydroxyl group to form an A ring hydroxylated apomorphine derivative.

22. The process of claim 17 further comprising: hydrogenating said stable halogen isotope to a hydrogen.

23. The process of claim 21 further comprising halogenating said A ring hydroxylated apomorphine derivative proximal to said hydroxyl group.

24. The process of claim 17 wherein the replacement of at least one of $R_{14}$, $R_{15}$, or $R_{16}$ with X occurs where X has a lower atomic weight than said stable halogen isotope.

25. The process of claim 24 wherein said X replacing $R_{14}$, $R_{15}$, or $R_{16}$ is a radioisotope.

26. The process of claim 17 wherein replacement of said stable halogen isotope comprises: forming a trialkyl stannous compound and reacting said trialkyl stannous with a compound containing said halogen isotope.

27. A commercial package comprising a compound of Formula I according to claim 1 as an active ingredient together with instructions for the use thereof as a radioimaging agent.

* * * * *